United States Patent
Harttig et al.

(10) Patent No.: US 8,821,399 B2
(45) Date of Patent: Sep. 2, 2014

(54) TAPE CASSETTE FOR A MEDICAL HANDHELD DEVICE

(75) Inventors: Herbert Harttig, Neustadt (DE); Juergen Braun, Ehningen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 372 days.

(21) Appl. No.: 12/967,458

(22) Filed: Dec. 14, 2010

(65) Prior Publication Data
US 2011/0166431 A1    Jul. 7, 2011

Related U.S. Application Data

(63) Continuation of application No. PCT/EP2009/003308, filed on May 9, 2009.

(30) Foreign Application Priority Data

Jun. 18, 2008    (EP) .................................... 08011015

(51) Int. Cl.
| | |
|---|---|
| A61B 5/00 | (2006.01) |
| B65D 81/00 | (2006.01) |
| G01N 31/00 | (2006.01) |
| A61B 5/151 | (2006.01) |
| A61B 5/15 | (2006.01) |
| G01N 21/75 | (2006.01) |
| G01N 31/22 | (2006.01) |
| A61B 5/145 | (2006.01) |

(52) U.S. Cl.
CPC ........... *A61B 5/1411* (2013.01); *A61B 5/15178* (2013.01); *A61B 5/15146* (2013.01); *A61B 5/15169* (2013.01); *A61B 2562/0295* (2013.01); *A61B 5/15171* (2013.01); *A61B 5/15148* (2013.01); *A61B 5/14532* (2013.01)

USPC ............. 600/309; 422/410; 422/430; 422/66; 600/365; 600/583; 600/584

(58) Field of Classification Search
USPC .................................. 600/309, 365, 583, 584
See application file for complete search history.

(56) References Cited

U.S. PATENT DOCUMENTS

| | | | |
|---|---|---|---|
| 3,244,287 | A | 4/1966 | Staunton et al. |
| 4,218,421 | A | 8/1980 | Mack, Jr. et al. |

(Continued)

FOREIGN PATENT DOCUMENTS

| | | |
|---|---|---|
| EP | 1424040 A1 | 6/2004 |
| WO | WO 2004/056269 A1 | 7/2004 |
| WO | WO 2005/047861 A2 | 5/2005 |
| WO | WO 2005/104948 A1 | 11/2005 |
| WO | WO 2008/083844 A1 | 7/2008 |
| WO | WO 2008/110267 A1 | 9/2008 |
| WO | WO 2008110267 A1 * | 9/2008 |

OTHER PUBLICATIONS

International Search Report dated Jun. 26, 2009 for PCT/EP2009/003308 (4 pages).

*Primary Examiner* — Dirk Bass
*Assistant Examiner* — Jennifer Wecker
(74) *Attorney, Agent, or Firm* — Faegre Baker Daniels LLP

(57) ABSTRACT

A tape cassette for a medical handheld device is disclosed as comprising a carrier tape, which carries test fields for assaying a sample of a human or animal bodily fluid and/or lancets as functional elements, a supply chamber, in which a supply section of the carrier tape comprising unused functional elements is positioned, a winding unit, in order to wind up the carrier tape and draw it through a tape exit opening of the chamber, so that the functional elements may be brought sequentially into a usage position. The carrier tape in the tape exit opening is oriented transversely to the supply section positioned in the supply chamber.

16 Claims, 1 Drawing Sheet

(56) References Cited

U.S. PATENT DOCUMENTS

| | | |
|---|---|---|
| 5,077,010 A | 12/1991 | Ishizaka et al. |
| 7,276,027 B2 * | 10/2007 | Haar et al. .................... 600/309 |
| 2005/0232815 A1 * | 10/2005 | Ruhl et al. ..................... 422/66 |
| 2005/0245845 A1 * | 11/2005 | Roe et al. ...................... 600/583 |
| 2006/0196504 A1 * | 9/2006 | Augustyn et al. ........ 128/203.15 |
| 2008/0286149 A1 * | 11/2008 | Roe et al. ........................ 422/58 |
| 2008/0300509 A1 * | 12/2008 | Hoenes et al. ................. 600/583 |
| 2010/0049090 A1 * | 2/2010 | Konya et al. .................. 600/583 |
| 2010/0198109 A1 * | 8/2010 | Harttig ........................... 600/583 |

\* cited by examiner

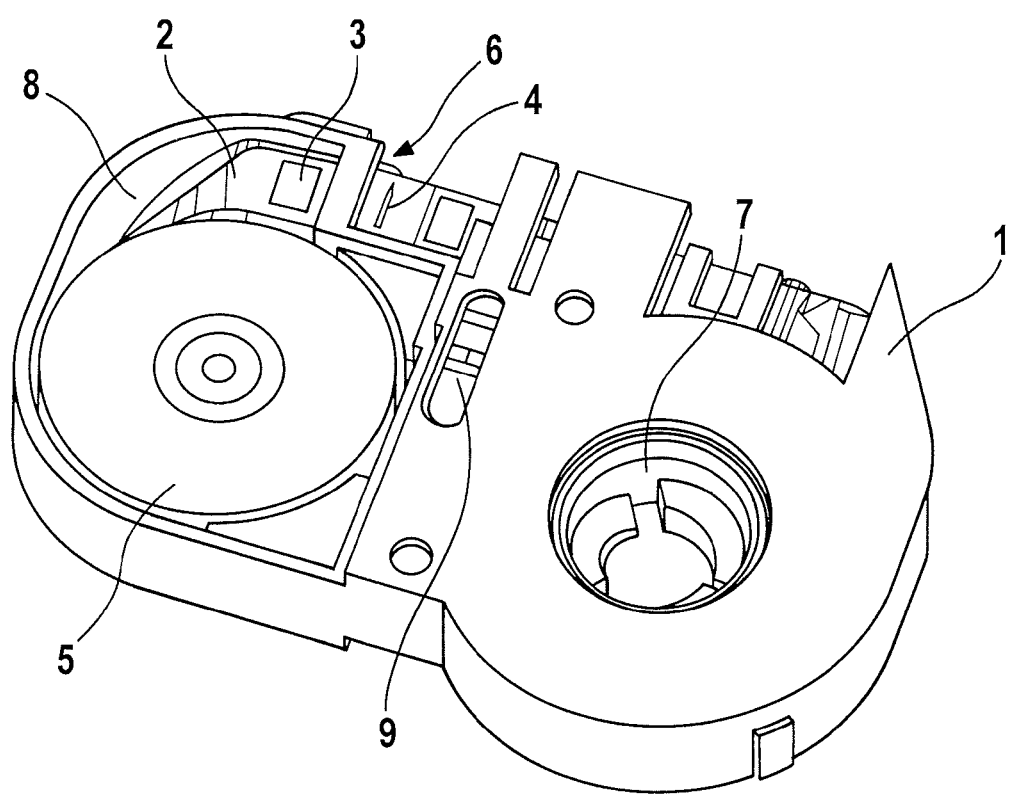

TAPE CASSETTE FOR A MEDICAL HANDHELD DEVICE

RELATED APPLICATIONS

The present application is a continuation of and claims priority to PCT/EP2009/003308, filed May 9, 2009, which claims priority to EP 08011015.8, filed Jun. 18, 2008, the entire disclosures of which being hereby expressly incorporated herein by reference.

FIELD OF THE DISCLOSURE

The disclosure relates to a tape cassette containing a carrier tape having functional elements, namely test fields for assaying bodily fluid samples and/or lancets. For use, such tape cassettes are inserted into a handheld device which is used to determine the presence or the concentration of an analyte, in particular the glucose concentration and/or for creating a puncture with a lancet in order to acquire a sample.

BACKGROUND AND SUMMARY OF THE DISCLOSURE

Unused functional elements of carrier tapes are easily damaged. Therefore a supply section of the carrier tape is positioned in a supply chamber of the tape cassette and thereby protected from harmful environmental influences. By winding the carrier tape with used functional elements on a winding unit, the carrier tape having unused functional elements is drawn through a tape exit opening of the supply chamber, so that unused functional elements reach a usage position successively.

Tape cassettes containing such carrier tapes are required in particular by diabetics, who must perform a measurement of the glucose concentration of a bodily fluid sample acquired by a lancet puncture, typically blood or interstitial liquid, several times a day.

Tape cassettes containing a carrier tape, which carries both test fields and also lancets as functional elements, are also known. Such tape cassettes are intended for integrated handheld devices which can be used both for a measurement of a bodily fluid sample and also for sample acquisition by puncturing with a lancet. However, simpler blood sugar measuring systems frequently comprises two separate handheld devices, namely a lancing device and a measuring device. Tape cassettes whose carrier tapes carry lancets as the functional elements are known for such lancing devices For high user comfort, in medical handheld devices as are used in particular by diabetics, the easiest possible tape transport is important. In simpler handheld devices, the tape transport is caused manually by the user, more complex handheld devices have an electric motor in order to bring the functional elements of the carrier tape into the usage position in sequence.

The present disclosure discloses a way in which the transport of a carrier tape can be made easier in a medical handheld device.

In a tape cassette according to the present disclosure, the carrier tape is oriented in the tape exit opening transversely to a supply section positioned in the supply chamber. This means that the tape plane is tilted in the tape exit opening in relation to the supply section positioned in the supply chamber. Surprisingly a significant reduction of friction can be caused by this apparently simple measure.

The supply section is preferably wound on a roller, so that the supply section is oriented parallel to a geometric rotational axis of the roller, while a tape section positioned in the tape exit opening is oriented transversely thereto, preferably perpendicularly to the geometric rotational axis of the roller. However, the supply section can also be folded into a stack. The tape plane of the tape section that is positioned in the tape exit opening is then oriented transversely to the tape plane of the folded supply section, preferably perpendicularly thereto.

A change of the orientation of the carrier tape in the supply chamber may be achieved by twisting the carrier tape. The carrier tape is preferably twisted by a quarter-turn in the supply chamber.

By orientating the carrier tape in the tape exit opening according to the present disclosure it is also possible to orient a section of the carrier tape having a functional element positioned in the usage position transverse to the geometric rotational axis of the winding unit. In this transverse section, lancets for executing a puncture may easily be moved transversely to the geometric rotational axis of the winding unit. In particular handheld devices having a lancing function may therefore be conceived as very flat, having a winding unit lying in the tape cassette, and may puncture a body part placed against a narrow side of the device, typically a finger, in an ergonomically advantageous manner.

The carrier tape preferably carries lancets between the test fields, so that the tape cassette is suitable for integrated handheld devices which can be used both for a measurement of a bodily fluid sample and for sample acquisition by puncturing with a lancet. If the carrier tape does not carry lancets, the test fields may be positioned at a distance from one another, adjoin one another, or even merge into one another, for example, in that the test fields are provided as a continuous strip.

Further details and features of the present disclosure are explained on an exemplary embodiment with reference to the appended drawing.

BRIEF DESCRIPTION OF THE DRAWING

FIG. 1 shows an embodiment of a tape cassette according to the invention.

DETAILED DESCRIPTION OF EMBODIMENTS OF THE DISCLOSURE

FIG. 1 shows an embodiment of a tape cassette with a partially open cassette housing 1. The tape cassette contains a carrier tape 2, which carries test fields 3 for assaying a sample of a human or animal bodily fluid. In the illustrated exemplary embodiment, lancets 4 are positioned between the test fields 3.

A supply section of the carrier tape 2 having unused test fields 3 is positioned in a supply chamber, in which the test fields 3 are protected from harmful environmental influences. In FIG. 1, a part of the housing 1 of the tape cassette which closes the supply chamber is removed, so that a freely rotatable roller 5, on which the supply section of the carrier tape 2 is wound, is visible.

Protection of the unused test fields 3 from harmful environmental influences is desirable, because test fields typically contain sensitive detection reagents, for example, for a photometric or electrochemical determination of an analyte concentration.

The supply chamber has a tape exit opening 6, through which the carrier tape 2 is guided. Used tape sections are wound on the winding unit 7. The winding unit 7 is positioned adjacent to the roller 5. The winding unit 7 is rotatable around a center which is positioned at a distance from the center of the roller 5, through which their geometric rotational axis runs, namely outside the supply chamber. This distance is greater than the diameter of the roller 5 when the carrier tape 2 is still unused.

During winding on the winding unit 7, carrier tape 2 is drawn out of the supply chamber, so that unused test fields 3 can be brought one after the other into a usage position to receive a sample. The usage position is on a line which is perpendicular to a connection line of the geometric rotational axis of the roller 5 and the geometric rotational axis of the winding unit 7. The winding unit 7 and the roller 5 are positioned in a plane.

A special feature of the illustrated embodiment is that the carrier tape 2 in the tape exit opening 6 is oriented transversely to the supply section positioned in the supply chamber. Specifically, in the supply chamber, the carrier tape 2 is twisted by a quarter-turn, so that the plane of the carrier tape ahead of the tape exit opening 6 is tilted by 90° in relation to the supply section wound on the winding roller 5.

This tilting of the tape plane is caused by a tape guide 8, which has a deflection bevel. The tape guide 8 can be implemented as a plastic block containing a desiccant. For friction reduction, the deflection bevel can have a surface made of a fluoropolymer, for example, PTFE or PVDF.

The tape exit opening 6 has a seal contacting the carrier tape 2, e.g. a sealing lip, in order to impede penetration of dust or other harmful environmental influences into the supply chamber.

On the way from the tape exit opening 6 to the winding unit 7, the carrier tape 2 is twisted by a further quarter-turn. This further quarter-turn can occur in the opposite direction to the quarter-turn in the supply chamber, i.e., cancel it out. However, the further quarter-turn preferably occurs in the same rotational direction as the quarter-turn in the supply chamber, so that the carrier tape 2 is twisted by a half-turn in total.

In the illustrated exemplary embodiment, a test field 3 positioned in the usage position having the associated carrier tape section is oriented transversely to the geometric rotational axis of the winding unit 7.

The lancets 4 positioned between the test fields 3 on the carrier tape 2 are oriented transversely to its longitudinal direction. In this manner, a drive of a handheld device in which the described tape cassette is used can execute a sample receiving or piercing movement transversely to the rotational axis of the winding unit 7. The tape cassette has a coupling unit 9, to which a drive of a handheld device can be coupled, in order to move the carrier tape 2 for receiving a sample or a lancet stick. When receiving a sample or during a lancing movement, a functional element positioned in the usage position, i.e., a test field 3 or a lancet 4, is moved together with a tape section carrying it in a direction which is in the tape plane of the tape section and is transverse to the tape's longitudinal direction.

Essentially the same movement can be performed for a lancet puncture or receiving a sample. During such a sample receiving or lancing movement, the front tape edge in the movement direction bends over, so that a lancet tip lifts off of the carrier tape 2 and can penetrate into a body part, which is placed on the handheld device. Such bending over of the front tape edge is also advantageous for receiving a sample using a test field 3 positioned in the usage position, because the surface pressing against the body part and thus against a sample exiting there is enlarged by the bending over.

What is claimed is:

1. A tape cassette for a medical handheld device, comprising:
    a carrier tape, which carries functional elements including at least one of test fields for assaying a sample of a human and/or animal bodily fluid and lancets;
    a supply chamber, in which a supply section of the carrier tape comprising unused functional elements is positioned;
    a winding unit configured to wind up the carrier tape and draw it through a tape exit opening of the supply chamber, thereby sequentially bringing the functional elements into a usage position; and
    a tape guide having a deflection bevel and being positioned in the supply chamber, the tape guide being configured to twist the carrier tape by a quarter-turn in the supply chamber such that the carrier tape in the tape exit opening is oriented transversely to an axis of rotation of the supply section positioned in the supply chamber.

2. The tape cassette according to claim 1, wherein the supply section of the carrier tape is wound on a roller.

3. The tape cassette according to claim 1, further including a desiccant positioned in the supply chamber.

4. The tape cassette according to claim 3, wherein the desiccant is contained in a plastic block, which forms the tape guide.

5. The tape cassette according to claim 1, wherein the deflection bevel has a surface made of a fluoropolymer.

6. The tape cassette according to claim 1, wherein the carrier tape is twisted by at least a quarter-turn between the usage position and the winding unit.

7. The tape cassette according to claim 1, wherein the carrier tape carries test fields and lancets positioned between the test fields.

8. The tape cassette according to claim 1, wherein the tape exit opening has a seal pressing against the carrier tape.

9. The tape cassette according to claim 1, wherein the winding unit is rotatable about a geometric axis, which runs transversely to a functional element positioned in the usage position.

10. The tape cassette according to claim 2, wherein the winding unit is positioned adjacent to the roller.

11. The tape cassette according to claim 2, wherein the winding unit is rotatable around a center, which is positioned at a distance from a center around which the roller is rotatable.

12. The tape cassette according to claim 2, wherein a geometric rotational axis of the winding unit is parallel to a geometric rotational axis of the roller.

13. A tape cassette for a medical handheld device, comprising:
    a carrier tape including a surface carrying a plurality of test fields for assaying a fluid sample and a plurality of lancets, each lancet being disposed adjacent a test field;
    a supply chamber configured to house a supply section of the carrier tape; and
    a winding unit configured to draw the supply section of the carrier tape out of the supply chamber through a tape exit opening of the supply chamber, thereby sequentially bringing the test fields and the lancets into a usage position whereby, when in the usage position, a plane of the carrier tape is positioned perpendicularly to a plane of the carrier tape when in the supply chamber.

14. The tape cassette according to claim 13, wherein the carrier tape is drawn onto the winding unit such that the surface of the carrier tape on the winding unit is positioned perpendicular to the surface of the carrier tape when in the usage position.

15. The tape cassette according to claim 13, wherein the supply section of the carrier tape is disposed on a roller having an axis of rotation that is substantially parallel to an axis of rotation of the winding unit.

16. A tape cassette for a medical handheld device, comprising:
- tape means for carrying a plurality of functional elements configured to assay a fluid sample;
- a roller on which a supply section of the tape means is wound; and
- means for winding the tape means thereby drawing the supply section of the tape means off of the roller and thus sequentially bringing the functional elements into a usage position wherein the tape means is oriented perpendicular to an orientation of an axis of rotation of the roller.

\* \* \* \* \*